(12) United States Patent
Kane et al.

(10) Patent No.: US 9,259,544 B2
(45) Date of Patent: Feb. 16, 2016

(54) PRESSURE SUPPORT SYSTEM WITH MACHINE DELIVERED BREATHS

(75) Inventors: Michael T. Kane, Harrison City, PA (US); Gregory Matthews, Pittsburgh, PA (US); Benjamin Irwin Shelly, Pittsburgh, PA (US); Heather Dawn Ressler, New Alexandria, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1064 days.

(21) Appl. No.: 13/201,937

(22) PCT Filed: Jan. 22, 2010

(86) PCT No.: PCT/IB2010/050292
§ 371 (c)(1),
(2), (4) Date: Aug. 17, 2011

(87) PCT Pub. No.: WO2010/097716
PCT Pub. Date: Sep. 2, 2010

(65) Prior Publication Data
US 2011/0303223 A1   Dec. 15, 2011

Related U.S. Application Data

(60) Provisional application No. 61/155,358, filed on Feb. 25, 2009.

(51) Int. Cl.
*F16K 31/02* (2006.01)
*A61M 16/00* (2006.01)

(52) U.S. Cl.
CPC ....... *A61M 16/00* (2013.01); *A61M 2016/0015* (2013.01)

(58) Field of Classification Search
None
See application file for complete search history.

(56) References Cited

U.S. PATENT DOCUMENTS

| | | | | |
|---|---|---|---|---|
| 5,134,995 | A * | 8/1992 | Gruenke et al. | 128/204.23 |
| 5,148,802 | A | 9/1992 | Sanders et al. | |
| 5,239,995 | A | 8/1993 | Estes et al. | |
| 5,313,937 | A | 5/1994 | Zdrojkowski | |
| 5,433,193 | A | 7/1995 | Sanders et al. | |
| 5,632,269 | A | 5/1997 | Zdrojkowski | |
| 5,803,065 | A | 9/1998 | Zdrojkowski et al. | |
| 5,845,636 | A * | 12/1998 | Gruenke et al. | 128/204.23 |
| 6,029,664 | A | 2/2000 | Zdrojkowski et al. | |
| 6,213,119 | B1 * | 4/2001 | Brydon et al. | 128/204.23 |
| 6,532,959 | B1 | 3/2003 | Berthon-Jones | |

(Continued)

FOREIGN PATENT DOCUMENTS

CN   1758931   4/2006
JP   2001259036 A   9/2001

(Continued)

*Primary Examiner* — Jason Flick
*Assistant Examiner* — Eric Bryant
(74) *Attorney, Agent, or Firm* — Michael W. Haas (57) ABSTRACT

A method of operating a ventilator or pressure support system that automatically determines a timed back up rate for the patient based on the patient's spontaneous breathing patterns. The aggressiveness of the determined rate increases as the patient takes less spontaneous breaths. Also, a method wherein one or more mechanisms are used to determine whether a machine breath should be issued. Each mechanism consists of a basic timing element coupled with one or more logical permits. Both the timing element and each of the one or more logical permits must be satisfied to allow the timing mechanism to trigger a machine breath.

23 Claims, 4 Drawing Sheets

(56) References Cited

U.S. PATENT DOCUMENTS

| | | | |
|---|---|---|---|
| 6,532,960 | B1 | 3/2003 | Yurko |
| 6,640,806 | B2 | 11/2003 | Yurko |
| 6,837,242 | B2 | 1/2005 | Younes |
| 6,920,875 | B1 | 7/2005 | Hill et al. |
| 7,246,618 | B2 * | 7/2007 | Habashi ............ 128/204.23 |
| 2005/0234364 | A1 * | 10/2005 | Kimmel et al. ......... 600/538 |
| 2006/0070624 | A1 | 4/2006 | Kane |
| 2006/0249148 | A1 | 11/2006 | Younes |
| 2007/0121524 | A1 * | 5/2007 | Rangarajan et al. ........ 370/252 |
| 2008/0071185 | A1 * | 3/2008 | Beck et al. .............. 600/529 |

FOREIGN PATENT DOCUMENTS

| | | | | |
|---|---|---|---|---|
| WO | WO9211054 | | 7/1992 | |
| WO | WO 2007/062400 | * | 5/2007 | ......... A61M 15/00 |

* cited by examiner

PRESSURE SUPPORT SYSTEM WITH MACHINE DELIVERED BREATHS

This patent application claims the priority benefit under 35 U.S.C. §119(e) of U.S. Provisional Application No. 61/155,358 filed on Feb. 25, 2009, the contents of which are herein incorporated by reference.

The present invention relates to positive airway pressure support systems, and, more particularly, to systems and methods for providing machine breaths to a patient using a pressure support system, including determining when a machine breath, which are also known as a timed breath or a backup breath, should be provided to the patient and determining minimum breath rates for use in providing pressure support therapy with automatic backup breaths.

It is known to utilize a pressure support system, such as a conventional ventilator, to deliver a fluid, such as oxygen, air or another oxygen or breathing gas mixture, to an airway of patient to augment or substitute the patient's own ventilatory effort. One basic form of pressure support therapy that may be provided by a ventilator is bi-level positive pressure therapy in which the pressure of gas delivered to the patient varies with the patient's breathing cycle. In a bi-level pressure support system, an inspiratory positive airway pressure (IPAP) is provided during a patient's inspiratory phase of the breathing cycle and an expiratory positive airway pressure (EPAP) is provided during the expiratory phase. The EPAP is lower than the IPAP to augment ventilation of the patient and so that the patient exhales against a relatively low pressure as compared to the IPAP pressure, thereby increasing the comfort to the patient. The BiPAP® family of pressure support devices manufactured by Respironics, Inc. of Murrysville, Pa., are examples of pressure support device that provide this bi-level form of pressure support therapy. In addition, several U.S. patents describe this bi-level pressure support system in detail, including U.S. Pat. Nos. 5,433,193; 5,313,937; 5,239,995; 5,148,802; 6,532,960; and 6,640,806, all of which are hereby expressly incorporated herein by reference as if set forth in their entirety herein.

It is further known to operate a conventional ventilator in a variety of modes to control the four basic operations of a ventilator, which are: 1) the trigger point, which is the transition from the expiratory to the inspiratory phase of the ventilatory cycle; 2) the inspiratory phase, where the ventilator delivers the flow of breathing gas; 3) the cycle point, which is the transition from the inspiratory phase to the expiratory phase, and 4) the expiratory phase where the patient exhales the delivered gas. There are four primary variables or parameters that are typically monitored and used to control how a ventilator performs one or more of these four operations. These variables are the volume, pressure, flow of fluid to or from the patient, and time.

In a typical life support situation, where there is substantially no spontaneous respiratory effort by the patient, a controlled mode of ventilation is provided, where the ventilator assumes full responsibility for ventilating the patient. In this mode of ventilation, the trigger and cycle point of the ventilator are determined based on time. In other situations, where the patient exhibits some degree of spontaneous respiratory effort, an assist mode or a support mode of ventilation is typically provided. Both of these modes of ventilation cause the ventilator to augment or assist in the patient's own respiratory efforts. In the assist mode, the determination of the ventilator trigger point is based on the action of the patient and the determination of the cycle point is determined based on time. In the support mode, both the trigger and the cycle points are patient based and not based on time.

Some patients capable of spontaneous breathing may nonetheless at times stop driving airflow for several seconds; the cause of this may take on several forms. An episode known as a central apnea occurs when the brain fails to instruct the body to take a breath. An episode known as an obstructive apnea occurs when the patient's airway collapses due to reduced tonality in the upper airway dilator muscles. In order to address such situations, it is also known to use a combination of the assist and control modes, referred to as an assist/control mode of ventilation or as S/T or Spontaneous/Timed mode of ventilation. In this mode of ventilation, the ventilator triggers an inspiratory flow (known variously as a backup breath, a timed breath or machine breath) if the patient fails to spontaneously initiate a respiratory effort for a period of time. Thus, in an assist/control mode of ventilation, the trigger point is based on either a patient action or on time (if there is no patient action within a certain period of time). In other words, during apneas, the ventilator recognizes the lack of spontaneous breathing activity and delivers a machine breath in order to drive tidal volume into the patient. This machine breath will allow gas exchange to occur and the deleterious effects of the apnea will be minimized.

In many patients, apneas only exist during some portion of the night; otherwise the patient demonstrates normal spontaneous breathing patterns. As noted above, ventilators currently available may be configured by the physician to deliver a timed breath whenever the patient's spontaneous rate has dropped below a predetermined and configured setting on the ventilator. These machines are typically designed to provide a minimum timed rate with a fixed time of inspiration. The device monitors the patient's spontaneous breathing rate and if the patient's spontaneous rate falls below the timed rate setting, the machine begins to deliver timed breaths at the rate setting. The ventilator delivers a machine breath with a fixed time of inspiration equal to the inspiratory setting the physician has selected.

One problem with current ventilators is that determining the optimal timed breath rate settings for each patient requires a trained technician. Often an overnight sleep study is required and the resulting settings only apply to the patient's current metabolic and pulmonary mechanics. As the patient's needs change, the settings can only be altered by the adjusting the settings on the ventilator.

Another problem with current ventilators is that they could deliver a timed breath even while the patient is still exhaling the previous breath. For example, if the ventilator logic monitors expiration to inspiration transitions (E to I transitions) and the timing is such that spontaneous rate has dropped below the ventilator setting, a machine breath could be issued even while the patient is actively exhaling, which condition is typically uncomfortable for the patient and causes breath stacking, a condition which increases the residual tidal volume the lungs and reduces the vital capacity for new breaths. Increasing the residual tidal volume also flattens the diaphragm which reduces the effectiveness of the patient's muscular effort to breathe.

In one embodiment, a method of providing pressure support to a patient is provided that includes steps of monitoring data relating to the respiratory activity of the patient, monitoring a timer, and determining that the timer has expired. After determining the timer has expired, the method further includes determining whether all of one or more logical permits are satisfied based on the data relating to respiratory activity of the patient, and providing a machine breath to the patient if it is determined that all of the one or more logical permits are satisfied.

In one particular embodiment, the one or more logical permits include a first logical permit relating to expiration of the patient, wherein the first logical permit will be determined to be satisfied if expiration of the patient is deemed to be complete. In another embodiment, the timer is a conservative timer that is triggered when an inspiration to expiration transition is detected, wherein the one or more logical permits in this embodiment include only the first logical permit.

In yet another particular embodiment, the timer is an aggressive timer that is triggered when an expiration to inspiration transition is detected, wherein the one or more logical permits in this embodiment are a plurality of logical permits. The plurality of logical permits may include a second logical permit relating to a percent of timed breaths over a predetermined number of prior breaths, such as the last 12 breaths, wherein the second logical permit will be determined to be satisfied if the percent of timed breaths over the predetermined number of prior breaths is less than a predetermined amount, such as 50%. Alternatively, the plurality of logical permits may include a second logical permit relating to minute ventilation, wherein the second logical permit will be determined to be satisfied if a short term minute ventilation measured over a first time period (e.g., 30 seconds) is less than a long term minute ventilation measured over a second time period (e.g., 120 seconds) longer than the first time period.

In another alternative, the plurality of logical permits includes a second logical permit relating to the standard deviation of prior breath periods over a predetermined period, wherein the second logical permit will be determined to be satisfied if the standard deviation is less than a predetermined value, such as 0.25. In still another alternative, the plurality of logical permits includes a second logical permit that will be determined to be satisfied if a flag is set to TRUE, wherein the flag is set to true when a timed breath is provided to the patient, and is set to FALSE only if three consecutive timed breaths are delivered to the patient. The permit flag may be set to TRUE again only after a spontaneous breath has occurred.

In yet another embodiment, a method of providing pressure support to a patient is provided that includes steps of monitoring a first timer, determining whether the first timer has expired, and if it is determined that the first timer has expired: (i) determining whether a first logical permit relating to expiration of the patient is satisfied, wherein the first logical permit will be determined to be satisfied if expiration of the patient is deemed to be complete, and (ii) providing a machine breath to the patient if it is determined that the first logical permit is satisfied. The method also includes steps of monitoring a second timer, determining whether the second timer has expired, and if it is determined that the second timer has expired: (i) determining whether all of a plurality of logical permits are satisfied, wherein the plurality of logical permits include the first logical permit, and (ii) providing a machine breath to the patient if it is determined that all of the plurality of logical permits are satisfied.

In a particular implementation of this method, the first timer is a conservative timer that is triggered when an inspiration to expiration transition is detected, and the method further comprises setting the first timer to a first timer value whenever an inspiration to expiration transition is detected, the first timer value being the lesser of: (i) an average time of expiration of the patient multiplied by a first constant, and (ii) a portion of a predetermined minimum breath period, and the second timer is an aggressive timer that is triggered when an expiration to inspiration transition is detected, and the method further comprises setting the second timer to a second timer value whenever an expiration to inspiration transition is detected, the second timer value being the lesser of: (i) an average breath period of the patient multiplied by a second constant, and (ii) a predetermined minimum breath period.

In still another embodiment, a method of providing pressure support to a patient is provided that includes determining a minimum breath rate based on data relating to the patient's prior spontaneous breathing, wherein the determined minimum breath rate is a function of an amount of the patient's prior spontaneous breathing relative to total breaths of the patient, and using the determined minimum breath rate in determining whether to provide a machine breath to the patient.

In a specific embodiment of the method, the determined minimum breath rate increases as the amount of the patient's prior spontaneous breathing relative to total breaths of the patient decreases. In a specific implementation, the data relating to the patient's prior spontaneous breathing comprises a percentage of prior breaths triggered by the patient, wherein the determined minimum breath rate increases as the percentage of prior breaths triggered by the patient decreases. In a more specific implementation, the determined minimum breath rate is a first rate if the percentage of prior breaths triggered by the patient is less than a first percentage, wherein the determined minimum breath rate is a second rate if the percentage of prior breaths triggered by the patient is greater than or equal to the first percentage but is less than a second percentage, and wherein the determined minimum breath rate is a third rate if the percentage of prior breaths triggered by the patient is greater than or equal to the second percentage. The first rate may be 10 BPM and the first percentage may 20%, the second rate may be 9 BPM and the second percentage may be 40%, and the third rate may be 8 BPM.

An exemplary embodiment of the present invention contemplates that the determined minimum breath rate is used to determine a timer value for a timer, wherein the timer is used in determining whether to provide the machine breath to the patient.

The present invention also contemplates implementing the techniques discussed above in a ventilator or pressure support system. For example, in one embodiment, the present invention contemplate providing a pressure support system that includes a means for monitoring data relating to respiratory activity of the patient, a timing means for determining that an elapsed period of time has expired, and a means, responsive to determining that the elapsed period of time has expired, for determining whether all of one or more logical permits are satisfied based on the data relating to respiratory activity of the patient. The system further includes a means for providing a machine breath to the patient if it is determined that all of the one or more logical permits are satisfied.

In a further embodiment, the ventilator or pressure support system includes a first timing means for determining whether a first time period has expired, and a means, responsive to a determination that the first period has elapsed, for (a) determining whether a first logical permit relating to expiration of the patient is satisfied, wherein the first logical permit will be determined to be satisfied if expiration of the patient is deemed to be complete, and for (b) providing a machine breath to the patient if it is determined that the first logical permit is satisfied. A second timing means is provided for determining whether a second time period has expired, as well as a means, responsive to a determination that the second period has elapsed, for (a) determining whether all of a plurality of logical permits are satisfied, wherein the plurality of logical permits include the first logical permit, and for (b) providing a machine breath to the patient if it is determined that all of the plurality of logical permits are satisfied.

In yet another embodiment, the system includes a means for determining a minimum breath rate based on data relating to the patient's prior spontaneous breathing, wherein the determined minimum breath rate is a function of an amount of the patient's prior spontaneous breathing relative to total breaths of the patient, and a means for determining whether to provide a machine breath to the patient based on the determined minimum breath rate.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

As employed, herein, the statement that two or more parts or components are "coupled" together shall mean that the parts are joined or operate together either directly or through one or more intermediate parts or components. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Figure 1:
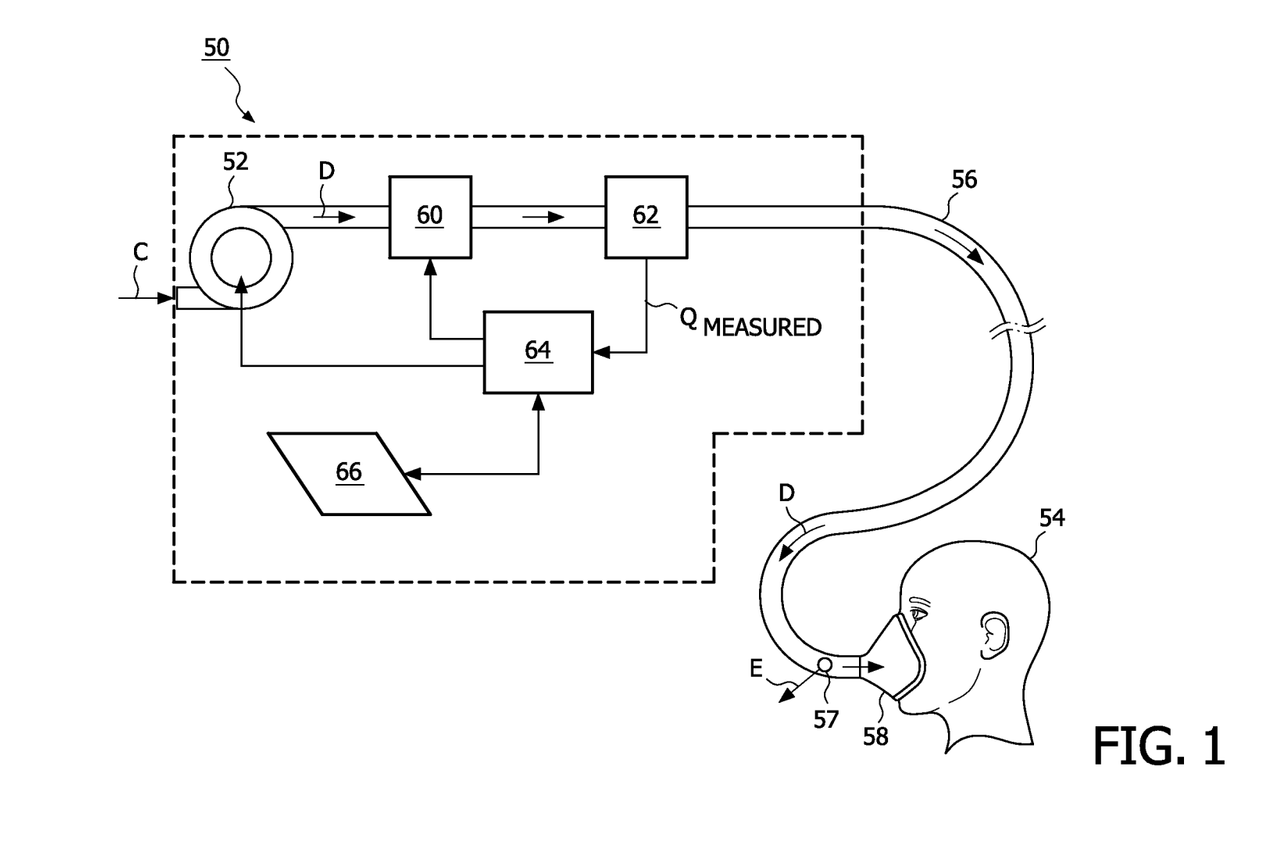
FIG. 1 a schematic diagram of pressure support system according to one particular, non-limiting embodiment of the invention.

As described in greater detail herein (i.e., following the description of pressure support system 50 in connection with FIG. 1), the present invention, in one particular embodiment, provides a ventilator and a method of operating a ventilator that automatically determines a timed back up rate for the patient. More specifically, the patient's spontaneous breathing patterns are analyzed by the ventilator and an optimal timed breath rate is calculated. Further, signal processing techniques are applied to determine if indeed a machine breath should be delivered to the patient.

As also described in greater detail herein (i.e., following the description of pressure support system 50 in connection with FIG. 1), in the exemplary embodiment there are two mechanisms which are used to determine whether a machine breath should be issued. Both mechanisms are evaluated simultaneously, and either mechanism may independently trigger a machine breath. Each mechanism consists of a basic timing element coupled with one or more logical permits. Both the timing element and each of the one or more logical permits must be satisfied to allow the timing mechanism to trigger the machine breath. The two mechanisms are unique to each other in that one is conservative in its timing of the machine breath and the other is aggressive in its timing of the machine breath. In the exemplary embodiment, the conservative mechanism has a long duration timing element and only a single logical element, and the aggressive mechanism has a short duration timing element and a more complex set of multiple logical permits.

FIG. 1 is a schematic diagram of pressure support system 50 according to one particular, non-limiting embodiment of the invention, which will be used herein to illustrate the present invention in its various embodiments. Referring to FIG. 1, pressure support system 50 includes gas flow generator 52, such as a blower used in a conventional CPAP or bi-level pressure support device, which receives breathing gas, generally indicated by arrow C, from any suitable source, e.g., a pressurized tank of oxygen or air or other gas or gas mixture, the ambient atmosphere, or a combination thereof. Gas flow generator 52 generates a flow of breathing gas, such as air, oxygen, or a mixture thereof, for delivery to an airway of patient 54 at relatively higher and lower pressures, i.e., generally equal to or above ambient atmospheric pressure.

The pressurized flow of breathing gas, generally indicated by arrow D from gas flow generator 52, is delivered via delivery conduit 56 to breathing mask or patient interface 58 of any known construction, which is typically worn by or otherwise attached to patient 54 to communicate the flow of breathing gas to the airway of patient 54. Delivery conduit 56 and patient interface device 58 are typically collectively referred to as a patient circuit. In one particular embodiment, patient interface 58 includes a pressure sensor operatively coupled to the controller 64 for measuring the pressure of gas that is delivered to the patient.

Pressure support system 50 shown in FIG. 1 is what is known as a single-limb system, meaning that the patient circuit includes only delivery conduit 56 connecting patient 54 to pressure support system 50. As such, exhaust vent 57 is provided in delivery conduit 56 for venting exhaled gasses from the system as indicated by arrow E. It should be noted that exhaust vent 57 can be provided at other locations in addition to or instead of in delivery conduit 56, such as in patient interface device 58. It should also be understood that exhaust vent 57 can have a wide variety of configurations depending on the desired manner in which gas is to be vented from pressure support system 50.

The present invention also contemplates that pressure support system 50 can be a two-limb system, having a delivery conduit and an exhaust conduit connected to patient 54. In a two-limb system (also referred to as a dual-limb system), the exhaust conduit carries exhaust gas from patient 54 and includes an exhaust valve at the end distal from patient 54. The exhaust valve in such an embodiment is typically actively controlled to maintain a desired level or pressure in the system, which is commonly known as positive end expiratory pressure (PEEP).

Furthermore, in the illustrated exemplary embodiment shown in FIG. 1, patient interface 58 is a nasal mask. It is to be understood, however, that patient interface 58 can include a nasal/oral mask, full face mask, nasal cannula, nasal pillows, tracheal tube, endotracheal tube, or any other device that provides a suitable gas flow communicating function. Also, for purposes of the present invention, the phrase "patient interface" can include delivery conduit 56 and any other structures that connect the source of pressurized breathing gas to patient 54.

In the illustrated embodiment, pressure support system 50 includes a pressure controller in the form of valve 60 provided in delivery conduit 56. Valve 60 controls the pressure of the flow of breathing gas from flow generator 52 delivered to patient 54. For present purposes, flow generator 52 and valve 60 are collectively referred to a pressure generating system because they act in concert to control the pressure and/or flow of gas delivered to patient 54. However, it should be apparent that other techniques for controlling the pressure of the gas delivered to patient 54, such as varying the blower speed of flow generator 52, either alone or in combination with a pressure control valve, are contemplated by the present invention. Thus, valve 60 is optional depending on the technique used to control the pressure of the flow of breathing gas delivered to patient 54. If valve 60 is eliminated, the pressure generating system corresponds to flow generator 52 alone, and the pressure of gas in the patient circuit is controlled, for example, by controlling the motor speed of flow generator 52.

Pressure support system 50 further includes flow sensor 62 that measures the flow of the breathing gas within delivery conduit 56. In the particular embodiment shown in FIG. 1, flow sensor 62 is interposed in line with delivery conduit 56, typically downstream of valve 60. Flow sensor 62 generates a flow signal $Q_{MEASURED}$ that is provided to controller 64 and is used by controller 64 to determine the flow of gas at patient 54, referred to as $Q_{PATIENT}$. Of course, other techniques for measuring the respiratory flow of patient 54 are contemplated by the present invention, such as, without limitation, measuring the flow directly at patient 54 or at other locations along delivery conduit 56, measuring patient flow based on the operation of flow generator 52, and measuring patient flow using a flow sensor upstream of valve 60.

Controller 64 may be, for example, a microprocessor, a microcontroller or some other suitable processing device, that includes or is operatively coupled to a memory (not shown) that provides a storage medium for data and software executable by controller 64 for controlling the operation of pressure support system 50, including automatically determining a timed back up rate for patient 54 and determining if indeed a machine breath should be delivered to patient 54 as described in greater detail below. Finally, input/output device 66 is provided for setting various parameters used by pressure support system 50, as well as for displaying and outputting information and data to a user, such as a clinician or caregiver. The present invention also contemplates that the timing functions and control of the backup breaths can be implemented in separate devices, i.e., separate processors or other separately dedicated components.

In an exemplary, non-limiting embodiment of the present invention, pressure support system 50 essentially functions as a bi-level pressure support system, and, therefore, includes all of the capabilities necessary in such systems in order to provide separate IPAP and EPAP levels to patient 54. This includes receiving the necessary parameters, via input commands, signals, instructions or other information, for providing a bi-level pressure, such as maximum and minimum IPAP and EPAP settings. The flow signal $Q_{MEASURED}$ from flow sensor 62 is also provided to controller 64, which controls pressure generating system 50 to output the desired inspiratory and expiratory waveforms. Typically, carrying out the pressure support operation includes estimating or determining the actual patient flow ($Q_{PATIENT}$) based on the flow signal $Q_{MEASURED}$, determining whether patient 54 is in the inspiratory or expiratory phase of the respiratory cycle and providing an I/E state signal (binary in form) indicative of the perceived respiratory state of patient 54 (I representing inspiratory phase and E representing expiratory phase), and triggering and cycling pressure support system 50.

Alternatively, a non-binary form of I/E state may be employed (e.g., a phase relationship of inspiration and expiration, and the device can determine how quickly to cycle it and whether to advance the phase itself by providing a timed breath (See U.S. Pat. No. 6,532,959, FIG. 3 and Col 9, line 33 to Col 10, line 54). In addition, in an exemplary embodiment, pressure support system 50 is adapted to implement an automatic backup process for providing machine breaths to patient 54 according to the methodology described herein. Thus, pressure support system 50 is able to provide control, assist, support, and assist/control modes of ventilation.

In one embodiment of the present invention, which is a single-limb system, controller 64 estimates the leakage of gas from the pressure support system using any conventional technique and incorporates this leak estimation into the determination of the actual patient flow. This leak estimation is required in a single-limb system, because a single-limb system includes a known leak through the exhaust vent as well as other unknown leaks, such as leaks at the patient contact site of the patient interface and at various conduit couplings on the patient circuit. In a two-limb system, leak estimation may not be required, because a flow sensor is typically provided at the exhaust vent to measure, directly, the flow of exhaust gas. In such a system, the patient flow can be determined by subtracting the measured exhaust flow from the measured flow delivered to the patient. It can be appreciated that leak detection can be performed in a two-limb system to increase the accuracy of the patient flow determination.

U.S. Pat. No. 5,148,802 to Sanders et al., U.S. Pat. No. 5,313,937 to Zdrojkowski et al., U.S. Pat. No. 5,433,193 to Sanders et al., U.S. Pat. No. 5,632,269 to Zdrojkowski et al., U.S. Pat. No. 5,803,065 to Zdrojkowski et al., U.S. Pat. No. 6,029,664 to Zdrojkowski et al., and U.S. Pat. No. 6,920,875 to Hill et al., the contents of each of which are incorporated herein by reference, are examples of patents that describe how to accomplish the functions used to provide separate IPAP and EPAP levels to the patient. These functions include techniques for detecting and estimating leak, and techniques for detecting the respiratory state of a patient (I/E), and managing, e.g., triggering and cycling, the bi-level delivery of breathing gas to the patient in the presence of leaks. Thus, a detailed discussion of these functions is omitted from the present application for the sake of simplicity and brevity.

As described in greater detail below, the methodology of the present invention employs certain parameters that are determined/updated based on data relating to the spontaneous breathing of patient 54 that is collected by controller 64. For clarity and ease of description, those parameters are first described below, and the purpose and function of each parameter will be more clearly understood from the description of the methodology that follows.

Specifically, controller 64 maintains a running value for average expiration time, $E_{T\text{-}avg}$, which is the average time of expiration (based on the I/E signal described above generated by controller 64) in a predetermined number of prior spontaneous breaths, such as the last 12 spontaneous breaths. The $E_{T\text{-}avg}$ is updated with each breath. Based on $E_{T\text{-}avg}$, controller 64 also maintains and updates with each breath a proportional average expiration time, $E_{prop}$, which is equal to some proportion of $E_{T\text{-}avg}$ (i.e., $E_{T\text{-}avg}$ multiplied by a constant). In a non-limiting embodiment, $E_{prop} = E_{T\text{-}avg} * 1.66$ (the constant=1.66). Controller 64 also maintains a running value for average breath period, $P_{avg}$, which is the average total breath time (based on the I/E signal described above generated by controller 64) in a predetermined number of prior spontaneous breaths, for example the last 12 spontaneous breaths. The $P_{avg}$ is updated with each breath. Based on $P_{avg}$, controller 64 also maintains and updates with each breath a proportional average breath period, $P_{prop}$, which is equal to some proportion of $P_{avg}$ (i.e., $P_{avg}$ multiplied by a constant). In a non-limiting exemplary embodiment, $P_{prop}=P_{avg}*1.33$ $P_{avg}$ (the constant=1.33).

In addition, controller 64 determines and updates a minimum breath rate, $R_{min}$, that is based on recent patient breathing activity. In particular, in an exemplary, non-limiting embodiment, $R_{min}$ is based on the recent percentage of patient triggered breaths (spontaneous breaths) as monitored and determined by controller 64. Specifically, the percentage of patient triggered breaths is calculated as the number of spontaneous breaths (i.e., non-machine breaths) divided by the total number of all breaths (spontaneous and machine) over a certain time period, multiplied by 100. A moving window of time is used to observe the two variables. A typical time period is approximately one minute. The $R_{min}$ of pressure support system 50 is adjusted according to how much patient 54 is reliant on pressure support system 50 for breathing support, and $R_{min}$ is increased as patient 54 becomes more reliant on pressure support system 50.

In one particular, non-limiting embodiment, $R_{min}$ is determined as follows:
(i) Percentage of Patient Triggered Breaths <20%, $R_{min}$=10 breaths per minute (BPM);
(ii) Percentage of Patient Triggered Breaths <40%, $R_{min}$=9 breaths per minute (BPM);
(iii) Otherwise, $R_{min}$=8 breaths per minute (BPM). Thus, if patient 54 is breathing 100% spontaneous breaths, $R_{min}$ will be 8 BPM. As patient 54 begins to have apneas and the percentage of patient triggered breaths decreases to between 40 and 20 percent, $R_{min}$ will be increased to 9 BPM. Finally, if the percentage of patient triggered breaths for patient 54 drops below 20%, $R_{min}$ will be increased to 10 BPM.

Figure 2:
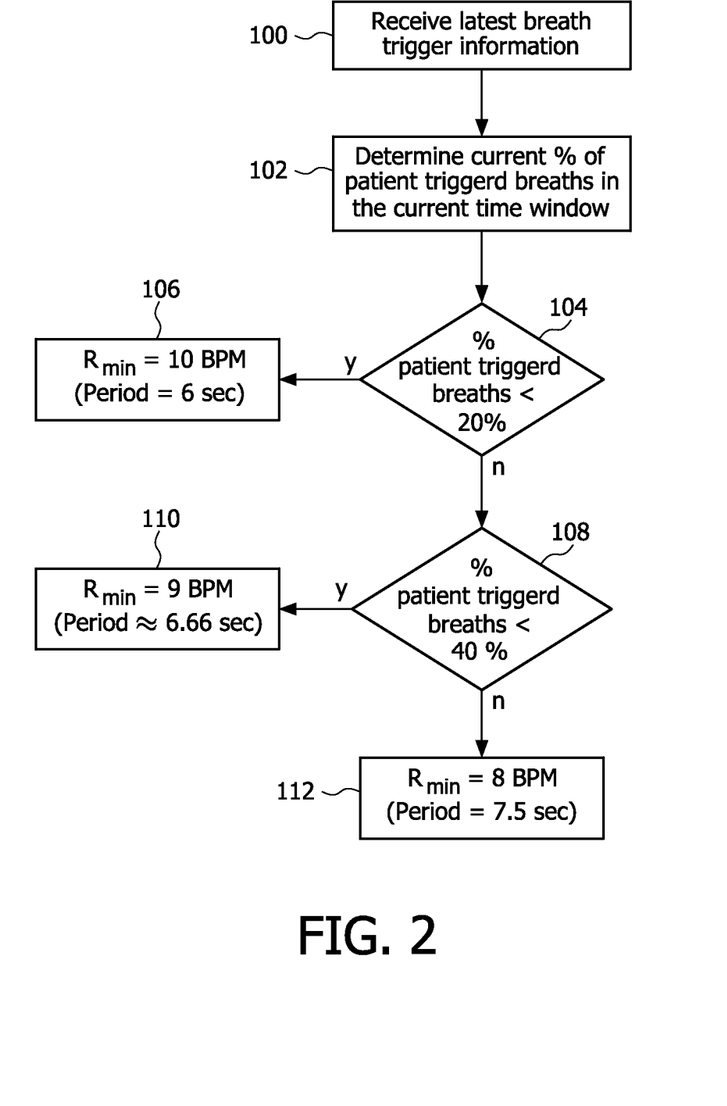
FIG. 2 is a flowchart that illustrates the determination of a minimum breath rate according to one particular embodiment of the invention.

FIG. 2 is a flowchart that illustrates the determination of $R_{min}$ according to this particular embodiment. At step 100, the routine in controller 64 that determines $R_{min}$ receives the latest breath trigger information which indicates whether the last breath was a patient triggered breath or a machine breath. At step 102, controller 64 determines the current percentage of patient triggered breaths, for example using the moving window approach described above. At step 104, a determination is made as to whether the current percentage of patient triggered breaths is less than 20%. If the answer is yes, then, at step 106, the current $R_{min}$ is set to 10 BPM, which equates to a breath period of 6 seconds. If the answer at step 104 is no, then, at step 108, a determination is made as to whether the current percentage of patient triggered breaths is less than 40%. If the answer is yes, then, at step 110, the current $R_{min}$ is set to 9 BPM, which equates to a breath period of approximately 6.66 seconds. If the answer at step 108 is no, then, at step 112, the current $R_{min}$ is set to 8 BPM, which equates to a breath period of 7.5 seconds. The breath period corresponding to each $R_{min}$ shall be referred to as $P_{min}$. It is to be understood that the particular percentages and the particular rates shown in FIG. 2 are just one particular embodiment, and that other percentages and/or rates may also be employed.

As noted elsewhere herein, in an exemplary embodiment there are two mechanisms which are used to determine whether a machine breath should be issued. Both mechanisms are implemented in controller 64 and are evaluated simultaneously; either mechanism may independently trigger a machine breath. Each mechanism consists of a basic timing element coupled with one or more logical permits. Both the timing element and each of the one or more logical permits must be satisfied to allow the timing mechanism to trigger the machine breath.

Figure 3:
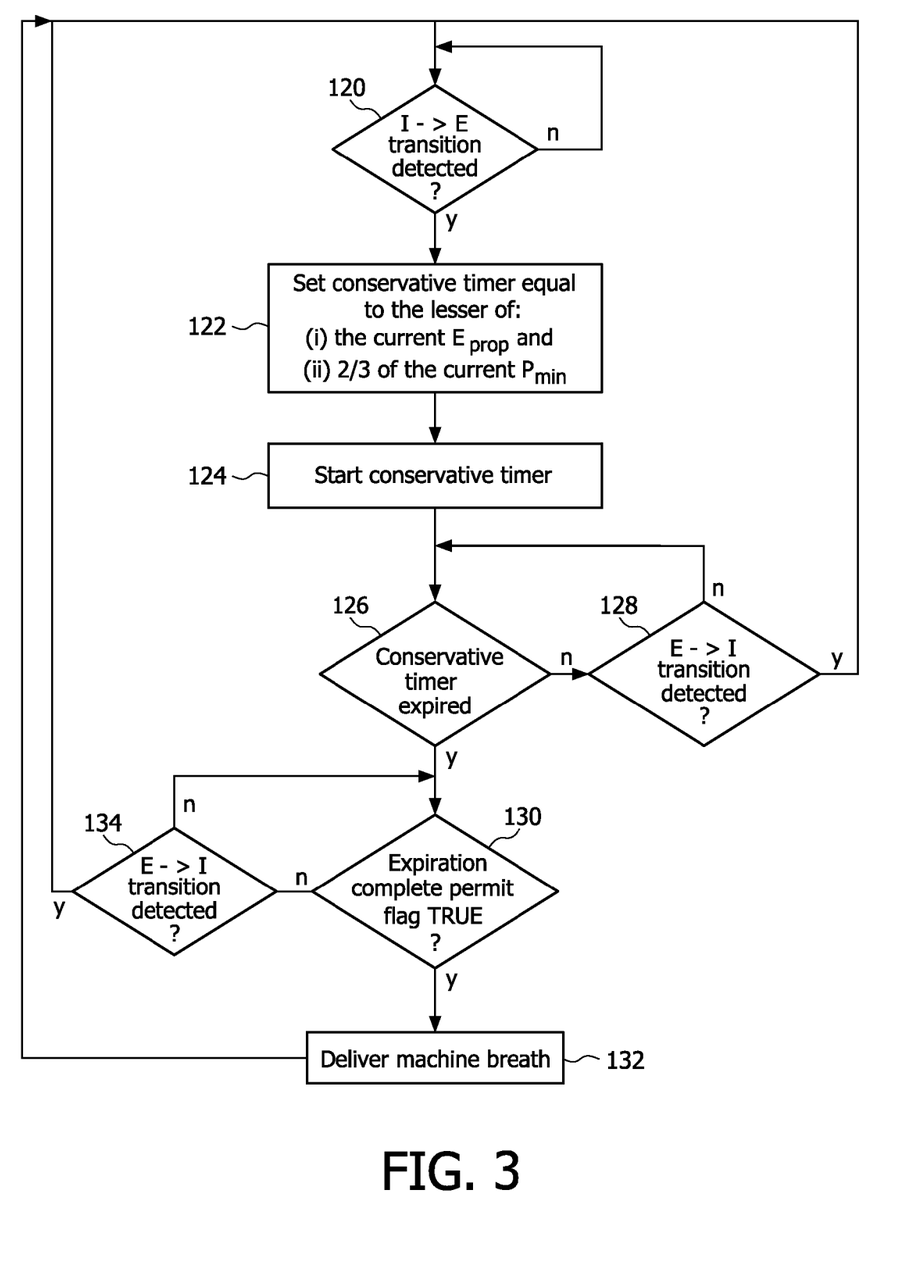
FIG. 3 is a flowchart that illustrates a first mechanism for determining whether a machine breath should be provided to the patient according to one particular embodiment of the invention.

The first mechanism, a particular embodiment of which is shown in the flowchart of FIG. 3, is a conservative mechanism based on time in exhalation. The timing element of the first mechanism, referred to herein as the conservative timer, has a duration equal to the lesser of: (i) the current $E_{prop}$, described above, and (ii) two-thirds (⅔) of the current $P_{min}$, and resets/starts (triggers) at I to E transitions (i.e., the beginning of the expiratory phase). In addition, the first mechanism employs only a single logical permit (namely, the Expiration Complete permit described below) which must be satisfied to allow the first mechanism to trigger a machine breath. Since the first mechanism evaluates exhalation time only, long inspiration times do not affect performance. More specifically, the benefits are two fold. Short inspiratory breaths cause little delay before this mechanism will initiate a timed breath for a patient that needs one, and long inspiratory times prolong the activation of this mechanism for patients who do not need one.

Figure 4:
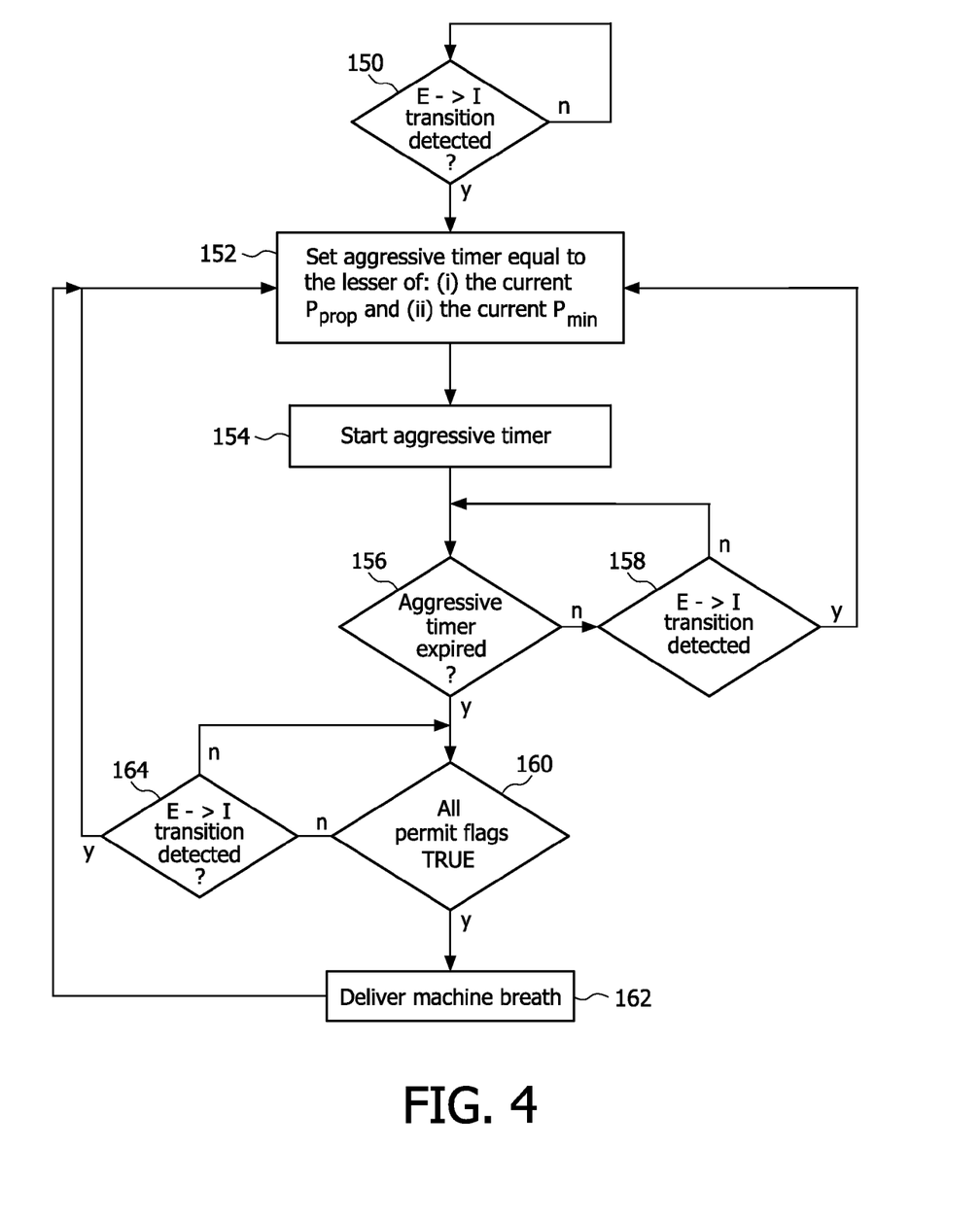
FIG. 4 is a flowchart that illustrates a second mechanism for determining whether a machine breath should be provided to the patient according to another particular embodiment of the invention.

The second mechanism, a particular embodiment of which is shown in the flowchart of FIG. 4, is an aggressive mechanism (relative to the conservative first mechanism since it is tuned to be slightly faster) based on breath period time. The timing element of the second mechanism, referred to herein as the aggressive timer, has a duration equal to the lesser of: (i) the current $P_{prop}$, described above, and (ii) the current $P_{min}$, and resets/starts (triggers) at E to I transitions (i.e., the beginning of the inspiratory phase). In addition, the second mechanism employs multiple logical permits described below that each must be satisfied to allow the second mechanism to trigger a machine breath.

Before describing the first (conservative) and second (aggressive) mechanisms in greater detail in connection with FIGS. 3 and 4, respectively, each of the logical permits employed in an exemplary embodiment of the present methodology will be described below.

The first logical permit is referred to herein as the Expiration Complete permit. This logical permit is the single logical permit used in the first (conservative) mechanism (it is also used as one of the multiple permits of the second (aggressive) mechanism). In the exemplary embodiment, the Expiration Complete permit analyzes the patient flow signal $Q_{patient}$, which is based on the $Q_{MEASURED}$ signal described elsewhere herein, over several seconds to observe a point in time when both the derivative of flow and the absolute value of flow are zero. In the exemplary embodiment, the patient flow is integrated into tidal volume and one second tidal volume "buckets" of tidal volume sum data are created. A derivative function examines the difference in tidal volume over last two "buckets." A static flow function looks at the absolute inspired tidal volume within the last second. For exhalation to be considered to be complete, both measures must be simultaneously less then 100 ml. Thus, an Expiration Complete permit flag will be set to TRUE whenever this condition is met and FALSE whenever this condition is not met. It should be noted that a moving window approach could also be used for this permit. In an alternative embodiment, a volume is integrated throughout the entire breath (from the patient flow signal), and exhalation is deemed complete where the volume expired matches the volume from the immediate preceding inspiration.

The second logical permit is referred to herein as the Recent Backup Breaths Issued permit. A Recent Backup Breaths Issued permit flag is set to TRUE when any timed breath (machine breath) has fired, and is set to FALSE whenever 3 timed breaths (machine breaths) have occurred. The Recent Backup Breaths Issued permit flag may be set to TRUE again only after a spontaneous breath has occurred.

The third logical permit is referred to herein as the Percent Timed Triggered Breaths Less Than 50% permit. In the exemplary implementation of this logical permit, a twelve position boxcar is used to monitor the percent of timed breaths over the last 12 breaths. Whenever the percent of timed breaths over the last 12 breaths is less than 50%, a Percent Timed Triggered Breaths Less Than 50% permit flag is set to TRUE. Otherwise, the flag is set to FALSE.

The fourth logical permit is referred to herein as the Short Term Minute Ventilation Less Than Long Term Minute Ventilation permit. This examines two moving windows of minute ventilation, one for short term minute ventilation measured using a window having a first length and one for long term minute ventilation measured using a window having a second length. In an exemplary, non-limiting embodiment, the first length is 30 seconds and the second length is 120 seconds. A Short Term Minute Ventilation Less Than Long Term Minute Ventilation permit flag is set to TRUE whenever the short term minute ventilation is less than the long term minute ventilation. Otherwise, the flag is set to FALSE.

The fifth logical permit is referred to herein as the No Recent Burst Breathing permit. The No Recent Burst Breathing permit examines a two minute window of data and compares the standard deviation of the breath periods of certain accepted breaths (i.e., only breaths that meet the specific criteria described below) to a threshold, and if the standard deviation is less than the threshold, then a No Recent Burst Breathing permit flag is set to TRUE, and otherwise it is set to False. In an exemplary embodiment, if the measured standard deviation is less than a threshold value of 0.25 seconds, the No Recent Burst Breathing permit flag is set to TRUE, otherwise it is False.

As noted above, before a particular breath can be used in the standard deviation calculation, it must meet certain criteria. In particular, there are two test criteria used to examine each particular breath, and at least one of the criteria must pass for the breath to be accepted. A first test is conducted to determine if the breath is normal. For a breath to be considered normal, all of the following acceptance tests must be True: (i) peak flow must be greater than 0; (ii) breath period must be greater than 2 seconds; (iii) time inspiration must be greater than 0.5 seconds; (iv) inhaled and exhaled tidal volume must be within 65% of each other; and (v) inhaled tidal volume must be greater than 150 ml. If all the above criteria are met, the breath is considered normal and accepted and a value of True is passed into second test as an input. If any of the above tests fail, then a value of False is passed into the second test as an input. The second test is passed the results from the first test. That is to say that values of True and False are passed into the second test. The second test monitors the occurrences of True and False to identify periods when large numbers of False values are being passed in. If 5 out of the last 10 breaths have first test False values, then the second test passes the current breath and zeros the internal counting mechanism.

FIG. 3 is a flowchart demonstrating the operation of the first (conservative) mechanism (implemented in controller 64) based on time in exhalation. As noted above, the timing element of the first mechanism (the conservative timer) resets/starts any time there is an I to E transition (i.e., the beginning of the expiratory phase) as determined by controller 64. Thus, operation begins at step 120, where a determination is made as to whether an I to E transition is detected. If the answer is no, the operation returns to step 120. If the answer is yes, meaning an I to E transition has been detected, then operation proceeds to step 122, wherein the conservative timer is set equal to the lesser of the current $E_{prop}$ and two-thirds (⅔) of the current $P_{min}$. Then at step 124, the conservative timer is started (countdown begins). At step 126, a determination is made as to whether the conservative timer has expired. If the answer is no, then, at step 128, a determination is made as to whether an E to I transition is detected (i.e., the beginning of inspiration for a breath (spontaneous or machine)). If the answer is yes, operation returns to step 120 (awaiting an I to E transition), and if the answer is no, operation returns to step 126 (monitoring expiration of the conservative timer).

If, however, the answer at step 126 is yes, meaning that the conservative timer has expired, then, at step 130, a determination is made as to whether the Expiration Complete permit flag is currently set to TRUE. If the answer is yes, then, at step 132, controller 64 causes a machine breath to be delivered according to predetermined parameters for the machine breath (e.g., inspiration time, IPAP level, EPAP level). In an exemplary embodiment, the inspiration time that is used for the machine breath is automatically determined and is equal to a calculated running average Time Insp. of spontaneous breaths (time of inspiration of spontaneous breaths). Following step 132, operation returns to step 120. If the answer at step 130 is no, then, at step 134, a determination is made as to whether an E to I transition is detected (i.e., the beginning of inspiration for a breath (spontaneous or machine)). If the answer is no, then operation returns to step 130 to monitor the state of the Expiration Complete permit flag. If, however, the answer at step 134 is yes, then operation returns to step 120 (awaiting an I to E transition).

FIG. 4 is a flowchart demonstrating the operation of the second (aggressive) mechanism (implemented in controller 64) based on breath period time. As noted above, the timing element of the second mechanism (the aggressive timer) resets/starts any time there is an E to I transition (i.e., the beginning of the inspiratory phase) as determined by controller 64. Thus, operation begins at step 150, where a determination is made as to whether an E to I transition is detected. If the answer is no, the operation returns to step 150. If the answer is yes, meaning an E to I transition has been detected, then operation proceeds to step 152, wherein the aggressive timer is set equal to the lesser of the current $P_{prop}$ and the current $P_{min}$. Then at step 154, the aggressive timer is started (countdown begins). At step 156, a determination is made as to whether the aggressive timer has expired. If the answer is no, then, at step 158, a determination is made as to whether an E to I transition is detected (i.e., the beginning of inspiration for a breath (spontaneous or machine)). If the answer is yes, operation returns to step 152 (timer reset), and if the answer is no, operation returns to step 156 (monitoring expiration of the aggressive timer).

If, however, the answer at step 156 is yes, meaning that the aggressive timer has expired, then, at step 160, a determination is made as to whether all of the permit flags described above (the Expiration Complete permit flag, the Recent Backup Breaths Issued permit flag, the Percent Timed Triggered Breaths Less Than 50% permit flag, the Short Term Minute Ventilation Less Than Long Term Minute Ventilation permit flag, and the No Recent Burst Breathing permit flag) are currently set to TRUE. If the answer is yes, then, at step 162, controller 64 causes a machine breath to be delivered according to predetermined parameters for the machine breath (e.g., inspiration time, IPAP level, EPAP level). In an exemplary embodiment, the inspiration time that is used for the machine breath is automatically determined and is equal to calculated a running average Time Insp. of spontaneous breaths (time of inspiration of spontaneous breaths). Following step 162, operation returns to step 152. If the answer at step 160 is no (one or more flags not TRUE), then, at step 164, a determination is made as to whether an E to I transition is detected (i.e., the beginning of inspiration for a breath (spontaneous or machine)). If the answer is no, then operation returns to step 160 to monitor the state of the permit flags. If, however, the answer at step 164 is yes, then operation returns to step 152 (timer reset).

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A method of providing pressure support to a patient, comprising:
    monitoring data relating to respiratory activity of the patient;
    monitoring a timer;
    determining that the timer has expired;
    after determining the timer has expired, determining whether all of one or more logical permits are satisfied based on the data relating to respiratory activity of the patient; and
    providing a machine breath to the patient if it is determined that all of the one or more logical permits are satisfied, wherein the one or more logical permits include a first logical permit relating to expiration of the patient and wherein the first logical permit will be determined to be satisfied if expiration of the patient is deemed to be complete, and wherein expiration of the patient is deemed to be complete in response to analyzing patient flow over a predetermined period and observing a point in time wherein both a derivative of the patient flow and an absolute value of the patient flow are less than a predetermined value.

2. The method according to claim 1, wherein the analyzing comprises integrating the patient flow into tidal volume data, and creating a plurality of tidal volume groups each corresponding to a predetermined duration from the tidal volume data, each tidal volume group comprising a sum of the tidal volume data of the tidal volume group, wherein at any particular point in time the derivative is determined by determining an absolute value of a difference between the sum for the tidal volume group associated with the particular point in time and the sum for the tidal volume group immediately preceding the tidal volume group associated with the particular point in time, and wherein the absolute value of the patient flow at the particular point in time is equal to the absolute value of the sum for the tidal volume group associated with the particular point in time.

3. The method according to claim 2, wherein the predetermined value is 100 ml.

4. The method according to claim 1, further comprising integrating the patient flow into tidal volume data, and creating a plurality of tidal volume groups each corresponding to a predetermined duration from the tidal volume data, each tidal volume group comprising a sum of the tidal volume data of the tidal volume group, wherein expiration of the patient is deemed to be complete in response to both: (i) determining that an absolute value of a difference between the sum for the tidal volume group associated with a particular point in time and the sum for the tidal volume group immediately preceding the tidal volume group associated with the particular point in time is less than a predetermined value, and (ii) determining that an absolute value of the sum for the tidal volume group associated with the particular point in time is less than the predetermined value.

5. The method according to claim 4, wherein the predetermined value is 100 ml.

6. A method of providing pressure support to a patient, comprising:
    monitoring data relating to respiratory activity of the patient;
    monitoring a timer;
    determining that the timer has expired;
    after determining the timer has expired, determining whether all of one or more logical permits are satisfied based on the data relating to respiratory activity of the patient; and
    providing a machine breath to the patient if it is determined that all of the one or more logical permits are satisfied, wherein the one or more logical permits include a first logical permit relating to expiration of the patient and wherein the first logical permit will be determined to be satisfied if expiration of the patient is deemed to be complete, wherein expiration of the patient is deemed to be complete in response to analyzing patient flow over a breath, the method further comprising determining a volume throughout the breath, and wherein exhalation is deemed complete where a first portion of the volume associated with expiration matches a second portion of the volume associated with inspiration immediately preceding the first portion.

7. A method of providing pressure support to a patient, comprising:
    monitoring data relating to respiratory activity of the patient;
    monitoring a timer;
    determining that the timer has expired;
    after determining the timer has expired, determining whether all of one or more logical permits are satisfied based on the data relating to respiratory activity of the patient; and
    providing a machine breath to the patient if it is determined that all of the one or more logical permits are satisfied, wherein the one or more logical permits include a first logical permit relating to expiration of the patient and wherein the first logical permit will be determined to be satisfied if expiration of the patient is deemed to be complete, wherein the timer is a conservative timer that is triggered when an inspiration to expiration transition is detected, and wherein the one or more logical permits include only the first logical permit; and
    setting the timer to a timer value whenever an inspiration to expiration transition is detected, the timer value being the lesser of: (i) an average time of expiration of the patient multiplied by a constant, and (ii) a portion of a predetermined minimum breath period.

8. The method according to claim 7, wherein the constant is 1.66 and the portion is two-thirds.

9. A method of providing pressure support to a patient, comprising:
    monitoring data relating to respiratory activity of the patient;
    monitoring a timer;

determining that the timer has expired;
after determining the timer has expired, determining whether all of one or more logical permits are satisfied based on the data relating to respiratory activity of the patient; and
providing a machine breath to the patient if it is determined that all of the one or more logical permits are satisfied, wherein the one or more logical permits include a first logical permit relating to expiration of the patient and wherein the first logical permit will be determined to be satisfied if expiration of the patient is deemed to be complete, wherein the timer is an aggressive timer that is triggered when an expiration to inspiration transition is detected, and wherein the one or more logical permits are a plurality of logical permits; and setting the timer to a timer value whenever an expiration to inspiration transition is detected, the timer value being the lesser of: (i) an average breath period of the patient multiplied by a constant, and (ii) a predetermined minimum breath period.

10. The method according to claim 9, wherein the constant is 1.33.

11. A method of providing pressure support to a patient, comprising:
monitoring data relating to respiratory activity of the patient;
monitoring a timer;
determining that the timer has expired;
after determining the timer has expired, determining whether all of one or more logical permits are satisfied based on the data relating to respiratory activity of the patient; and
providing a machine breath to the patient if it is determined that all of the one or more logical permits are satisfied, wherein the one or more logical permits include a first logical permit relating to expiration of the patient and wherein the first logical permit will be determined to be satisfied if expiration of the patient is deemed to be complete, wherein the timer is an aggressive timer that is triggered when an expiration to inspiration transition is detected, and wherein the one or more logical permits are a plurality of logical permits, wherein the plurality of logical permits includes a second logical permit relating to a percent of timed breaths over a predetermined number of prior breaths, and wherein the second logical permit will be determined to be satisfied if the percent of timed breaths over the predetermined number of prior breaths is less than a predetermined amount.

12. The method according to claim 11, wherein the predetermined amount is 50%.

13. A method of providing pressure support to a patient, comprising:
monitoring data relating to respiratory activity of the patient;
monitoring a timer;
determining that the timer has expired;
after determining the timer has expired, determining whether all of one or more logical permits are satisfied based on the data relating to respiratory activity of the patient; and
providing a machine breath to the patient if it is determined that all of the one or more logical permits are satisfied, wherein the one or more logical permits include a first logical permit relating to expiration of the patient and wherein the first logical permit will be determined to be satisfied if expiration of the patient is deemed to be complete, wherein the timer is an aggressive timer that is triggered when an expiration to inspiration transition is detected, and wherein the one or more logical permits are a plurality of logical permits, wherein the plurality of logical permits includes a second logical permit relating to minute ventilation, and wherein the second logical permit will be determined to be satisfied if a short term minute ventilation measured over a first time period is less than a long term minute ventilation measured over a second time period longer than the first time period.

14. The method according to claim 9, wherein the plurality of logical permits includes a second logical permit relating to a standard deviation of prior breath periods over a predetermined period, and wherein the second logical permit will be determined to be satisfied if the standard deviation is less than a predetermined value.

15. A method of providing pressure support to a patient, comprising:
monitoring data relating to respiratory activity of the patient;
monitoring a timer;
determining that the timer has expired;
after determining the timer has expired, determining whether all of one or more logical permits are satisfied based on the data relating to respiratory activity of the patient; and
providing a machine breath to the patient if it is determined that all of the one or more logical permits are satisfied, wherein the one or more logical permits include a first logical permit relating to expiration of the patient and wherein the first logical permit will be determined to be satisfied if expiration of the patient is deemed to be complete, wherein the timer is an aggressive timer that is triggered when an expiration to inspiration transition is detected, and wherein the one or more logical permits are a plurality of logical permits, wherein the plurality of logical permits includes a second logical permit that will be determined to be satisfied if a flag is set to TRUE, and wherein the flag is set to true when a timed breath is provided to the patient, and is set to FALSE only if three consecutive timed breaths are delivered to the patient.

16. The method according to claim 7, wherein the predetermined minimum breath period is determined based on a percentage of prior breaths triggered by the patient.

17. The method according to claim 9, wherein the predetermined minimum breath period is determined based on a percentage of prior breaths triggered by the patient.

18. A method of providing pressure support to a patient, comprising:
monitoring a first timer, wherein the first timer is a conservative timer that is triggered when an inspiration to expiration transition is detected, the method further comprising setting the first timer to a first timer value whenever an inspiration to expiration transition is detected;
determining whether the first timer has expired;
if it is determined that the first timer has expired: (i) determining whether a first logical permit relating to expiration of the patient is satisfied, wherein the first logical permit will be determined to be satisfied if expiration of the patient is deemed to be complete, and (ii) providing a machine breath to the patient if it is determined that the first timer has expired and that the first logical permit is satisfied;
monitoring a second timer, wherein the second timer is an aggressive timer that is triggered when an expiration to inspiration transition is detected, the method further comprising setting the second timer to a second timer value whenever an expiration to inspiration transition is detected;

determining whether the second timer has expired;

if it is determined that the second timer has expired: (i) determining whether all of a plurality of logical permits are satisfied, wherein the plurality of logical permits include the first logical permit, and (ii) providing a machine breath to the patient if it is determined that the second timer has expired all of the plurality of logical permits are satisfied.

19. The method according to claim 17, wherein the first timer value is the lesser of: (i) an average time of expiration of the patient multiplied by a first constant, and (ii) a portion of a predetermined minimum breath period, and wherein the second timer value is the lesser of: (i) an average breath period of the patient multiplied by a second constant, and (ii) a predetermined minimum breath period.

20. The method according to claim 19, wherein the first constant is 1.66, the second constant is 1.33, and the portion is two-thirds.

21. A system of providing pressure support to a patient, comprising:

first timing means for determining whether a first time period has expired, wherein the first timing means is a conservative timer that is triggered when an inspiration to expiration transition is detected, first timing means being set to a first timer value whenever an inspiration to expiration transition is detected;

first permit means, responsive to a determination that the first time period has expired, for (a) determining whether a first logical permit relating to expiration of the patient is satisfied, wherein the first logical permit will be determined to be satisfied if expiration of the patient is deemed to be complete, and for (b) providing a machine breath to the patient responsive to determining that the first time period has expired and that the first logical permit is satisfied;

second timing means for determining whether a second time period has expired, wherein the second timing means is an aggressive timer that is triggered when an expiration to inspiration transition is detected, the second timing means being set to a second timer value whenever an expiration to inspiration transition is detected;

second permit means, responsive to a determination that the second time period has expired, for (a) determining whether all of a plurality of logical permits are satisfied, wherein the plurality of logical permits include the first logical permit, and for (b) providing a machine breath to the patient responsive to determining that the second time period has expired and that all of the plurality of logical permits are satisfied.

22. The system according to claim 21, wherein the first timer value is the lesser of: (i) an average time of expiration of the patient multiplied by a first constant, and (ii) a portion of a predetermined minimum breath period, and wherein the second timer value is the lesser of: (i) an average breath period of the patient multiplied by a second constant, and (ii) a predetermined minimum breath period.

23. The system according to claim 22, wherein the first constant is 1.66, the second constant is 1.33, and the portion is two-thirds.

* * * * *